United States Patent [19]

Krishnan et al.

[11] Patent Number: 5,622,687
[45] Date of Patent: Apr. 22, 1997

[54] CALIXARENE CONJUGATES USEFUL AS MRI AND CT DIAGNOSTIC IMAGING AGENTS

[75] Inventors: Ashwin M. Krishnan, San Diego; Rolf Lohrmann, La Jolla, both of Calif.

[73] Assignee: Molecular Biosystems, Inc., San Diego, Calif.

[21] Appl. No.: 340,206

[22] Filed: Nov. 15, 1994

[51] Int. Cl.$^6$ .................................................. A61B 5/055
[52] U.S. Cl. .................... 424/9.33; 424/9.36; 424/9.364; 424/9.37; 514/492; 514/502; 514/836; 436/173; 128/653.4; 128/654
[58] Field of Search .................... 424/9.33, 9.36, 424/9.364, 9.37; 514/492, 502, 836; 436/173; 128/653.4, 654

[56] References Cited

U.S. PATENT DOCUMENTS

| | | | |
|---|---|---|---|
| 4,474,747 | 10/1984 | Dimo et al. | 424/5 |
| 4,834,964 | 5/1989 | Rosen | 424/9 |
| 4,863,717 | 9/1989 | Keana | 424/9 |
| 4,873,075 | 10/1989 | Counsell et al. | 424/1.1 |
| 4,925,649 | 5/1990 | Counsell et al. | 424/1.1 |
| 5,006,663 | 4/1991 | Berchadsky et al. | 548/412 |
| 5,104,641 | 4/1992 | Rosen | 424/9 |
| 5,116,599 | 5/1992 | Rogers, Jr. et al. | 424/9 |
| 5,130,119 | 7/1992 | Blaszkiewicz et al. | 424/9 |
| 5,177,261 | 1/1993 | McCarthy et al. | 564/153 |
| 5,183,654 | 2/1993 | Speck et al. | 424/5 |
| 5,191,120 | 3/1993 | Kneller et al. | 564/153 |
| 5,204,086 | 4/1993 | Wille | 424/5 |
| 5,232,685 | 8/1993 | Speck et al. | 424/5 |
| 5,233,995 | 8/1993 | Yudelson et al. | 128/662.02 |
| 5,234,680 | 8/1993 | Rogers, Jr. et al. | 424/9 |
| 5,256,397 | 10/1993 | Rosen | 424/9 |
| 5,316,757 | 5/1994 | Sherry et al. | 424/9 |
| 5,324,504 | 6/1994 | Rogers, Jr. et al. | 424/9 |
| 5,338,532 | 8/1994 | Tomalia et al. | 424/1.49 |
| 5,401,493 | 3/1995 | Lohrmann et al. | 424/9 |

FOREIGN PATENT DOCUMENTS

| | | | |
|---|---|---|---|
| WO90/00904 | 2/1990 | WIPO | A61K 49/00 |
| WO92/08725 | 5/1992 | WIPO | C07F 9/6515 |
| WO93/10824 | 6/1993 | WIPO | A61K 49/04 |
| WO93/10825 | 6/1993 | WIPO | A61K 49/04 |
| WO94/03164 | 2/1994 | WIPO | A61K 31/18 |

OTHER PUBLICATIONS

Weinmann, H. et al., "Characteristics of Gadolinium–DTPA Complex: A Potential NMR Contrast Agent." *Am. J. Roentgen.* 142:619–24 (1984).
Le Mignon, M. et al., "Pharmacokinetics and Tolerability After Intravenous Injection into Healthy Volunteers." *Invest. Radiol.* 25:933–7 (1990).
Brasch, R.C. et al., "Work in Progress: Nuclear Magnetic Resonance Study of a Paramagnetic Nitroxide Contrast Agent for Enhancement of Renal Structures in Experimental Animals." *Radiology* 147(3):773–9 (1983).
Neiderl, J.B. et al., "Aldehyde–Resorcinol Condensations." *J. Amer. Chem. Soc.* 62:2512–4 (1940).
Gutsche, C.D., *Calixarenes*, Royal Society of Chemistry, pp. 1–223 (1992).

Asfari, Z. et al., "Calixarenes." *Janssen 24 Chimica Acta*, 10(1):3–9 (1992).
Bakker, W.I.I. et al., "Functionalized Calixspherands: Synthesis and Peptide Coupling." *J. Org. Chem.* 59:972–6 (1994).
Katzberg, R.W., *The Contrast Media Manual*, William & Wilkins, pp. 66–82, 143–160 (1992).
Gutsche, C.D. et al., "The Synthesis of Functionalized Calixarenes." *Tetrahedron* 42(6):1633–40 (1986).
Shinkai, S. et al., "Hexasulfonated Calix[6]arene Derivatives: A New Class of Catalysts, Surfactants, and Host Molecules." *J. Amer. Chem. Soc.* 108:2409–16 (1986).
Shinkai, S. et al., "Synthesis and Inclusion Properties of 'Neutral' Water–Soluble Calixarenes." *Bull. Chem. Soc. Jpn.* 63(4):1272–4 (1990).
Shinkai, S. et al., "Syntheses and Aggregation Properties of New Water–soluble Calixarenes." *J. Chem. Soc. Perkin Trans.* 1:2039–45 (1989).
Almi, M. et al., "Chloromethylation of Calixarenes and Synthesis of New Water Soluble Macrocyclic Hosts." *Tetrahedron* 45(7):2177–82 (1989).
McOmie, J.F.W. et al., "Dimethylation of Aryl Methyl Ethers by Boron Tribromide." *Tetrahedron* 24:2289–92 (1968).
Essien, H. et al., "Synthesis of Diethylenetriaminepentaacetic Acid Conjugated Inulin and Utility for Cellular Uptake of Liposomes." *J. Med Chem.* 31:898–91 (1988).
Betebenner, D.A. et al., "Hepatobiliary Delivery of Polyaminopolycarboxylate Chelates: Synthesis and Characterization of a Cholic Acid Conjugate of EDTA and Biodistribution and Imaging Studies with Its Indium–111 Chelate." *Bioconjugate Chem.* 2:117–23 (1991).
Mirzadeh, S. et al., "Radiometal Labeling of Immune Proteins: Covalent Linkage of 2–(4–Isothiocyanatobenzyl) diethylenetriaminepentaacetic Acid Ligands to Immunoglobulin" *Bioconjugate Chem.* 1:59–65 (1990).
Wiener, E.C. et al., "Dendrimer–Based Metal Chelates: A New Class of Magnetic Resonance Imaging Contrast Agents." *Mag. Reson. Med.* 31:1–8 (1994).

*Primary Examiner*—Gary E. Hollinden
*Attorney, Agent, or Firm*—Morrison & Foerster

[57] ABSTRACT

Calixarene conjugates useful for imaging, particularly magnetic resonance imaging (MRI) and computed tomography (CT) are described. Said calixarene conjugates comprise (i) a calixarene backbone, and (ii) at least one imaging moiety linked thereto, and may be of the formula:

$$\left[ \begin{array}{c} R^1 \\ \phantom{X} \\ R^4 \end{array} \text{—J—} \right]_n \quad (II)$$

wherein at least one of the $R^1$ and $R^4$ substituents comprises an imaging moiety, the remaining $R^1$ and $R^4$ substituents are spectator groups, J is an ortho-linker, and n is an integer from 4 to 8. Imaging moieties useful for CT imaging include those comprising two or more iodine atoms. Imaging moieties useful for MRI include (i) organic moieties comprising four or more fluorine atoms; (ii) nitroxyl spin labeled moieties; and (iii) metal chelate moieties.

17 Claims, 5 Drawing Sheets

CALIXARENE CONJUGATES USEFUL AS MRI AND CT DIAGNOSTIC IMAGING AGENTS

TECHNICAL FIELD

This invention relates to diagnostic imaging agents which are useful for magnetic resonance imaging (MRI) and computed tomography (CT).

BACKGROUND

Medical diagnostic imaging has evolved as an important non-invasive tool for the evaluation of pathological and physiological processes. Presently, nuclear magnetic resonance imaging (MRI) and computerized tomography (CT) are two of the most widely used imaging modalities. Although both MRI and CT can be performed without the administration of contrast agents, the ability of many contrast agents to enhance the visualization of internal tissues and organs has resulted in their widespread use.

Proton MRI is based on the principle that the concentration and relaxation characteristics of protons in tissues and organs can influence the intensity of a magnetic resonance image. Contrast agents which are useful for proton MRI effect a change in the relaxation characteristics of protons which can result in image enhancement and improved soft-tissue differentiation. Different classes of proton MR imaging agents include paramagnetic metal chelates and nitroxyl spin labelled compounds.

Two commercially available paramagnetic chelates are PROHANCE (Squibb Diagnostics, Princeton, N.J.) and MAGNEVIST (Berlex, Wayne, N.J.). (See also, inter alia, H. J. Weineman et al., *Am. J. Roentgenol.* 142:619–624, 1984; M. M. Le Mignon, et al., *Investigative Radiology* 25:933, 1990; A. D. Sherry et al., U.S. Pat. No. No. 5,316,757, issued 1994; and A. D. Sherry et al., PCT Application Ser. No. WO 92/08725, published 1992.)

Examples of nitroxyl spin labeled compounds are described by R. C. Brasch et al., *Radiologoy* 147:773–779, 1983; G. M. Rosen, U.S. Pat. No. 4,834,964, issued 1989; G. M. Rosen et al., U.S. Pat. No. 5,104,641, issued 1992; J. F. W. Keana et al., U.S. Pat. No. 4,863,717 issued 1989; G. M. Rosen, U.S. Pat. No. 5,256,397 issued 1993; Y. Berchadsky et al., U.S. Pat. No. 5,006,663, issued 1991; and I. B. Leunback, PCT Application Ser. No. WO 90/00904, published 1990.

Fluorine ($^{19}$F) MRI is also in the early stages of development. Because of the 100% natural abundance of $^{19}$F and the complete absence of biological background, $^{19}$F MRI promises to be an important diagnostic imaging tool of the future. Fluorine-containing imaging agents include perfluoro-tert-butyl containing organic compounds (W. J. Rogers, Jr., et al., U.S. Pat. Nos 5,116,599 issued 1992, 5,234,680 issued 1993, and 5,324,504 issued 1994) and fluoro-substituted benzene derivatives (P. Blaszkiewicz et al., U.S. Pat. No. 5,130,119 issued 1992.)

CT is based on the principle that various substances effect different degrees of attenuation of an X-ray beam. Contrast agents useful for CT usually contain atoms which are electron dense, such as bromine or iodine, and are efficient attenuators of X-ray radiation. By far the most common CT agents are monomeric or dimeric iodinated benzene rings with various pendent groups such as ORAGRAFIN, CHOLOGRAFIN and RENOGRAFIN (Squibb Diagnostics, Princeton, N.J.). One important advance in the use of iodine-containing CT agents has been the development of non-ionic contrast agents, such as the ones described by M. T. Kneller et al., PCT Application Ser. No. WO 93/10825 published 1993.

The usefulness and efficiency of chemical compounds as contrast agents depends on their ability to exhibit a predictable and desirable biodistribution and metabolism in vivo. Their behavior in vivo depends on parameters such as molecular weight, charge, osmolality, hydrophobicity, partition coefficient, susceptibility to metabolic breakdown, and tissue or organ targeting efficiency. In order to improve their solubility and biodistribution, many contrast agents are used in conjunction with delivery systems such as emulsions, liposomes, and microparticles. Others are combined with polymeric systems which allow complex contrast agents to be designed with specific molecular weight, charge and targeting characteristics. For example, contrast agents can be conjugated to dense star polymers (see, for example, Tomalia et al., U.S. Pat. No. 5,338,532, issued 1994) or amino acid polymers (D. Meyer, et al., PCT WO 93/10824, published 1993).

The present invention relates to novel CT and MRI agents which are in the form of calixarene conjugates. Calixarenes are macrocycles comprising phenolic units ortho-linked by methylene bridges, as represented by the following formula:

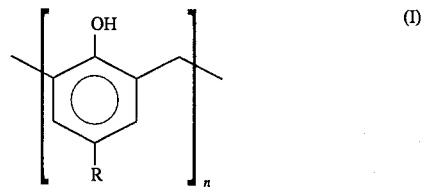

(I)

wherein n is typically 4, 5, 6, 7, or 8, and more commonly 4, 6, or 8. Calixarenes are commonly referred to as calix[n]arenes wherein n refersto the number of phenolic units. As denoted herein, the phenolic —OH group occupies the 1-position, and the substituent —R group occupies the 4-position. Although different conformations are possible depending on the type and degree of derivatization, calixarenes are often described as being basket- or cup-shaped, with a larger diameter upper rim comprised of substituents at the 4-positions and a smaller diameter lower rim comprised of substituents at the 1-positions.

Calixarenes were first discovered in the 1940's (see, inter alia, J. B. Niederl et al., *J. Am. Chem. Soc.*, 62:2512–2514, 1940). A variety of calixarenes and calixarene derivatives have been prepared and characterized (see, inter alia, C. D. Gutsche, *Calixarenes*, 1989, Royal Society of Chemistry, Cambridge, UK; and Z. Asfari et al., *Jansen* 24 Chimica Acta, 10(1):3–10,1992) and include, for example, alternative substituents at the 1-and/or 4-positions, and alternative ortho-linkages, such as —(C=O)—, —CH$_2$CH$_2$—, and —CH(CH$_3$)—.

Calixarenes have found use in catalysis (polymerization accelerators), transport and extraction of metallic cations (cesium ion extraction, metal ion sequestrants), and in modifying the chemical properties of polymers, drugs, and dyes (see, inter alia, Z. Asfari etal., supra; and W. I. Hwang etal., PCT Application Ser. No. WO 94/03164 published 1994).

Recently, Bakker etal. (*J. Org. Chem.*, 59:972–976, 1994) have disclosed the synthesis of radionuclidic "catixspherands", which are capable of forming stable complexes with radionuclides such as $^{81}$Rb$^+$. These calixspherands are composed of a calixarene backbone which is conjugated to a m-terphenyl moiety. The m-terphenyl moiety is subsequently derivatized and linked to a low molecular weight protein (LMWP) which facilitates organ (in this case, kidney) targeting. The calixspherand-LMWP conjugate thus formed is then complexed with $^{81}Rb^+$ and used in conjunction with a scintillation detection for the determination of blood flow in tissue and organs.

Heretofore, the use of calixarene conjugates as MRI or CT imaging agents has not been reported.

Disclosure of the Invention

The present invention relates to calixarene conjugates useful for imaging, particularly magnetic resonance imaging (MRI) and computed tomography (CT).

Accordingly, one aspect of the invention relates to calixarene conjugates comprising: (i) a calixarene backbone; and (ii) at least one imaging moiety linked thereto. Preferably, at least one imagining moiety is an MR imaging moiety or a CT imaging moiety.

Another aspect of the invention relates to calixarene conjugates of the formula:

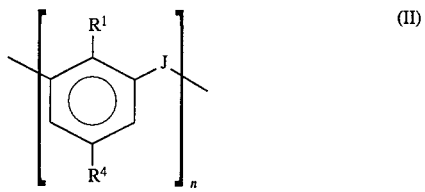

(II)

wherein at least one of the $R^1$ and $R^4$ substituents comprises an imaging moiety, the remaining $R^1$ and $R^4$ substituents, if any, are spectator groups, J is an ortho-linker, and n is an integer from 4 to 8.

Yet another aspect of the invention relates to calixarene conjugates useful for CT imaging wherein the imaging moiety comprises two or more iodine atoms.

Still another aspect of the invention relates to calixarene conjugates useful for MRI wherein the imaging moiety comprises at least one of (i) an organic moiety comprising four or more fluorine atoms; (ii) a nitroxyl spin labeled moiety; or (iii) a metal chelate moiety.

Yet another aspect of the invention relates to imaging agent formulations comprising a calixarene conjugate comprising a calixarene backbone and at least one CT or MR imaging moiety linked thereto, and a pharmaceutically acceptable carrier.

Still another aspect of the invention relates to methods of CT and/or MR imaging comprising the steps of (i) administering an effective amount of a calixarene conjugate of the invention; and (ii) acquiring a CT and/or MR image of the subject while the calixarene conjugate is present in the body.

DETAILED DESCRIPTION OF THE INVENTION

Figure 1:
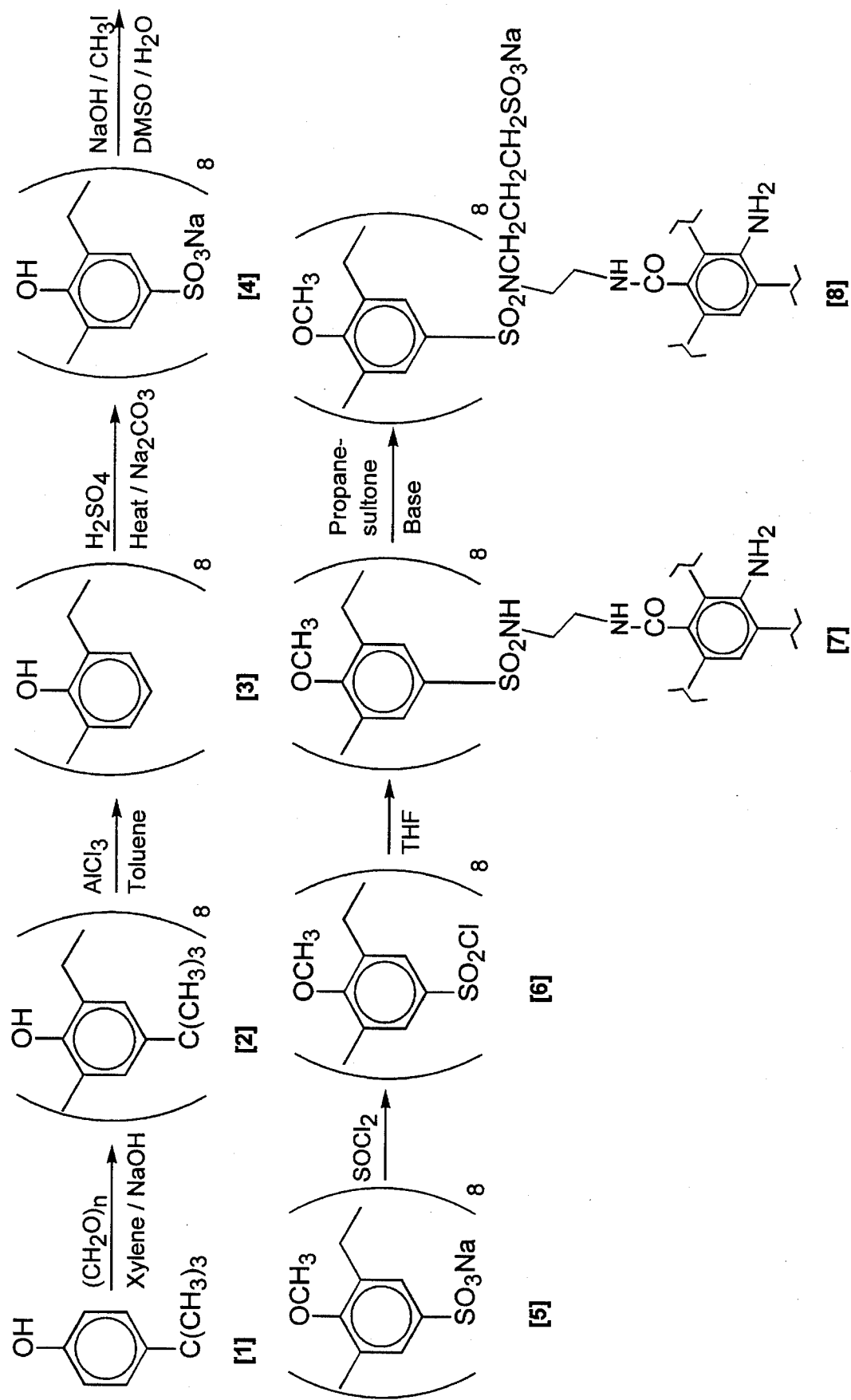
FIG. 1 is a flow chart that illustrates a synthetic route for the preparation of a calixarene conjugate having an iodinated CT imaging moiety.

The invention relates to imaging agents that enhance diagnostic images generated by magnetic resonance imaging (MRI) and computerized tomography (CT). These agents are comprised of calixarenes which have been conjugated to one or more imaging moieties to form calixarene conjugate imaging agents.

The terms listed below, as used herein, shall have the following meaning:

Calixarene:
  Macrocyclic compound comprised of ortho-linked phenolic units. Also included in the term "calixarenes" are derivatives of calixarenes such as those which result from the substitution and/or derivatization of the —OH in the 1-position.

Calix[n]arene:
  A calixarene wherein n refers to the number of phenolic units in the macrocycle.

Calixarene Conjugate Imaging Agent:
  A calixarene which is conjugated to at least one imaging moiety.

Calixarene Backbone:
  The calixarene portion of a calixarene conjugate imaging agent.

Imaging Agent:
  A compound containing at least one imaging moiety which, when administered to a subject, alters or enhances a diagnostic image of a part of the subject.

Imaging Moiety:
  The functional portion of an imaging agent which contains the chemical entity that alters or enhances the diagnostic image.

Linker Group:
  The chemical moiety which serves to covalently attach one or more imaging moieties to the calixarene.

Ortho-Linker:
  The linkage between phenolic units of a calixarene wherein the ortho-carbon of one phenyl group is linked to the ortho-carbon of the adjacent phenyl group.

A. Calixarene conjugates

The calixarene conjugate imaging agents of the present invention are described by the following formula:

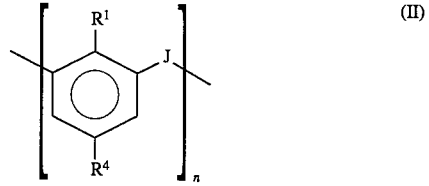

(II)

wherein $R^1$ is a substituent at the 1-position, $R^4$ is a substituent at the 4-mosimion, J is the ortho-linker between adjacent phenyl groups of the calixarene backbone, and n is an integer from 4 to 8, preferably 4, 6 or 8, more preferably 4 or 8, most preferably 8.

At least one of the $R^1$ or $R^4$ groups comprises an imaging moiety. It is contemplated that the imaging moiety portion of the calixarene conjugate imaging agent may comprise an MRI or CT imaging agent. When more than one of the $R^1$ or $R^4$ groups comprise an imaging moiety, the groups may be the same or different, but are preferably the same. Each $R^1$ and $R^4$ group may also contain more than one imaging moiety, in which case the imaging moieties may be the same or different, but are preferably the same.

Those $R^1$ and $R^4$ groups which do not comprise an imaging moiety instead comprise a spectator substituent. The spectator substituent is a pharmacologically acceptable group and may be chosen to enhance synthetic ease, water solubility, ionic charge, neutrality, and the like. The term "pharmacologically acceptable", as used herein, denotes a substituent which is inactive or innocuous in vivo. Examples of spectator substituents include, for example, the —OH group in the 1-position of simple calixarenes, which may be left unchanged, or may be derivatized to a different spectator substituent, such as O—CH$_3$.

Further examples of spectator substituents include —H; alkyl (linear, branched, or cyclic) of 1 to 15 carbon atoms, more preferably 1–6 carbon atoms, yet more preferably methyl; phenyl or substituted phenyl of 6 to 20 carbon atoms, such as aryl; aralkyl of 7 to 20 carbon atoms, more preferably substituted benzyl; alkaryl of 7 to 20 carbon atoms such as substituted phenyl; —OH; alkoxy of 1 to 10 carbon atoms, more preferably 1 to 6 carbon atoms, yet more preferably methoxy; carboxylic acid such as —CO$_2$H or —(CH$_2$)$_m$—CO$_2$H, wherein m is 1 to 4; sulfonic acid such as —SO$_3$H or —(CH$_2$)$_m$—SO$_3$H; amino acid such as —H—(CH$_2$)$_m$—CO$_2$H wherein m is as defined above; sulfonic acid amine such as —NH—(CH$_2$)$_m$—SO$_3$H, wherein m is as defined above; ethanolamine groups, such as —NHCH$_2$CH$_2$OH and —N(CH$_2$CH$_2$OH)$_2$; and amide such as —NHC(=O)R$^s$, —NR$^s$C(=O)R$^s$, —C(=O)NHR$^s$, or —C(=O)N(R$^s$)$_2$, wherein R$^s$, which may be the same or different, is also a pharmacologically acceptable group. The spectator substituent is preferably —H, alkyl, alkylsulfonate, alkylcarboxylate (with alkyl of 1–7 carbon atoms), aminoalkylamide (—C(=O)NH(CH$_2$)$_m$NH$_2$, wherein m is as defined above); and pharmacologically acceptable salts thereof. See, inter alia, Yudelson, et al., 1993, U.S. Pat. No. 5,233,995; Speck et al., 1993, U.S. Pat. No. 5,232,685; Speck et al., 1993, U.S. Pat. No. 5,183,654; McCarthy et al., 1993, U.S. Pat. No. 5,177,261; Willie, 1993, U.S. Pat. No. 5,204,086; Kneller et al., 1993, U.S. Pat. No. 5,191,120; Dimo et al., 1984, U.S. Pat. No. 4,474,747; and references therein.

The term "salt" as used herein denotes both suitable metal ion and organic ion salts. Suitable pharmacologically acceptable salts include metal ions, for example, alkali and alkaline earth cations, preferably Na$^+$, K$^+$, Mg$^{+2}$, and Ca$^{+2}$, more preferably Na$^+$ and K, and organic ions, for example, stable cationic and anionic species such as halide ion, preferably Cl$^-$ or Br$^-$, N-methylglucamine ("meglumine") cation, and tris(hydroxymethyl)amino methane ("TRIS") cation.

The imaging moieties are covalently attached to calixarenes via a linker group. In some instances, it may be possible to link one or more imaging moieties directly to a calixarene via a covalent bond, in which case a linker group or groups is/are not necessary. Examples of linker groups include, for example, amide (—NH—C(=O)—), sulfonamide (—NH—S(=O)$_2$—), thiourea (—NHC(=S)—NH—), urea (—NH—C(=O)—NH—), disulfide (—SS—), thioether (—S—), amidine (—NH—C(=NR)—), and carbamate (—NH—C(=O)—O—) linkages, and are preferably amide, sulfonamide, thiourea, and urea linkages.

The ortho-linker, J, is a chemical moiety which covalently joins together the phenyl groups of the calixarene backbone. Examples of ortho-linkers include —(CH$_2$)$_p$—, —(C=O)—, —CHR—, —(S=O)—, —(P=O)—, preferably —CH$_2$—, —(C=O)—, and —CHR—, and more preferably —CH$_2$—, wherein R is a hydrocarbyl, such as alkyl of 1 to 4 carbon atoms, preferably methyl, and p is an integer from 1 to 4, preferably 1 to 2.

CT imaging agents and the imaging moieties they are comprised of are either more or less electron dense than the tissues or organs being imaged so as to increase the differentiation therebetween. They are most typically electron beam opacifiers, also known as radiopaques, such as bromine or iodine-containing compounds, preferably the latter. CT imaging moieties preferably comprise two or more iodine atoms, more preferably three or more iodine atoms. A wide variety of CT imaging agents are known in the art (see, inter alia, *Radiographic Contrast Agents*, R. E. Miller et al., 1977, University Park Press, Baltimore, Md.). Iodine-containing compounds suit. able as sources of CT imaging moieties include, for example, polyiodinated phenyis, more preferably triiodinated phenyls, of the following general formula:

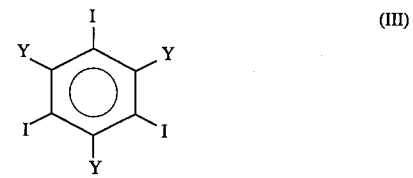

wherein Y is a pharmacologically acceptable group, as described above.

Additional iodine-containing compounds suitable as sources of CT imaging moieties include, for example, polyiodinated phenyl dimers of the following general formula:

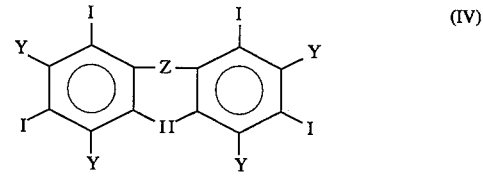

wherein Y is as defined above and Z is a linking group, including, for example, —NH—C (=O)—(CH$_2$)$_q$—C(=O)—NH—and —C(=O)—NH—(CH$_2$)$_q$—NH—C(=O)—, wherein q is 0 to 4, more preferably 0 to 2 (see, inter alia, *Radiographic Contrast Agents*, Miller et al., 1977, supra; Kneller et al., 1993, supra; Dimo et al., 1984, supra; and references therein).

MR imaging agents and the imaging moieties they are comprised of typically are substances that have magnetic properties which cause the brightening or darkening of a magnetic resonance image. Several different classes of MR imaging agents/imaging moieties are known. Among them are fluorine-containing organic compounds, nitroxyls, and paramagnetic metal chelates. Fluorine-containing imaging moieties of choice possess more than three magnetically equivalent fluorine atoms, more preferably six or more magnetically equivalent fluorine atoms, most preferably nine or more magnetically equivalent fluorine atoms. As used herein, the term "magnetically equivalent" denotes atoms present in a moiety or compound which yield magnetic resonance signals of a sufficiently similar frequency that they form a single resonance peak as detected by typical diagnostic magnetic resonance imaging apparati (see, for example, Rogers et al., 1993, U.S. Pat. No. 5,234,680).

A variety of fluorine-containing compounds suitable for use as imaging moieties are known in the art (see, inter alia, Rogers et al., U.S. Pat. No. 5,116,599, 1992 and 5,234,680, 1993) and include, for example, compounds possessing the perfluoro-tert-butyl group, such as C(CF$_3$)$_3$—(CH$_2$)$_r$—NH$_2$;

$C(CF_3)_r$—$(CH_2)_r$—$C(=O)X$; $C(CF_3)_3$—$(CH_2)_r$—X; 3,5-di(perfluoro-tert-butyl-methyl)benzoyl halide; and 4-perfluoro-tert-butyl-methylbenzoyl halide; wherein r is 1 to 5, preferably 2 to 4, and X (halide) is Cl, Br, or I, preferably Cl or Br. Additional examples of suitable fluorine-containing compounds are those possessing two or more perfluoromethyl groups, such as 3,5-di(trifluoromethyl)benzoyl halide, wherein halide is Cl, Br, or I, preferably Cl or Br.

Nitroxyl-containing imaging moieties include nitroxyl spin labels (NSP). Such moieties typically are organic, possess at least one nitroxyl (—N—O•) free radical, and are paramagnetic by virtue of having one unpaired electron. Nitroxyl-containing imaging moieties may be derived from the wide variety of piperidine-based NSP compounds which are known in the art (see, inter alia, Keana, 1989, U.S. Pat. No. 4,863,717; Berchadsky et al., 1991, U.S. Pat. No. 5,006,663; Leunback, 1990, WO 90/00904; and references therein) and include, for example, the piperidinoxyl moiety derived from 1,4-dihydroxy-2,2,6,6-tetramethylpiperidine, as shown below.

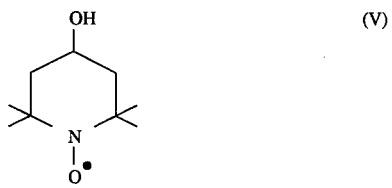

(V)

Additional nitroxyl-containing imaging moieties may be derived from pyrrole-based NSP compounds which are known in the art (see, inter alia, Rosen, 1993, U.S. Pat. No. 5,256,397; Rosen, 1992, U.S. Pat. No. 5,104,641; Berchadsky et al., 1991, supra; Rosen, 1989, supra; and Leunback, 1990, supra; and references therein) and include, for example, 2,2,5,5-pyrrolinidyl-oxyl compounds of the following formula, wherein $R^A$ is a carboxylalkyl or aminoalkyl group, and $R^s$, which may be the same or different, is an alkyl group.

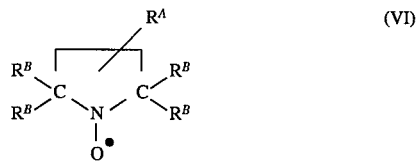

(VI)

Further nitroxyl-containing imaging moieties may be derived from tert-butyl-based NSP compounds which are known in the art (see, inter alia, Rosen, 1992, supra; and references therein) and include, for example, nitroxides of the following formula, wherein $R^c$, which may be the same or different, is alkyl, preferably methyl.

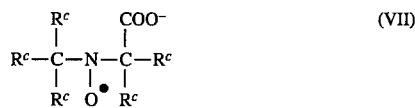

(VII)

Another class of MR imaging moieties useful for conjugation to calixarenes is the paramagnetic metal chelates. Metal chelate imaging moieties may be derived from paramagnetic metal complex MR imaging agents which are known (see, inter alia, Sherry et al., 1992, WO 92/08725, Sherry et al., 1994, U.S. Pat. No. 5,316,757, and references therein). Useful MRI calixarene conjugate imaging agents may be prepared by conjugating a chelating moiety to a calixarene backbone and subsequently forming a chelate-complex between the chelating moiety and a paramagnetic metal. Alternatively, calixarene conjugate imaging agents may be prepared by first forming a paramagnetic metal-complex between a chelating moiety and a paramagnetic metal and subsequently conjugating the paramagnetic metal-complex to a calixarene backbone.

The term "paramagnetic metals" as used herein denotes metal atoms or ions which are paramagnetic by virtue of one or more unpaired electrons, and excludes radioactive metal atoms or ions commonly referred to as radionuclides. Examples of paramagnetic metals used in MR imaging agents of the invention include the paramagnetic transition metals and lanthanides of groups 1b, 2b, 3a, 3b, 4a, 4b, 5b, 6b, 7b, and 8, more preferably those of atomic number 21–31, 39–50, 57–71, and 72–82, yet more preferably Gd, Dy, Cr, Fe, and Mn, still more preferably Gd, Mn, and Fe, and most preferably Gd.

The term "chelating moieties" as used herein denotes chemical moieties which are able to form chelate-complexes with paramagnetic metals. Examples of linear chelating moieties used in such MR imaging agents include the polyamino polyethylene polyacetic acids (e.g. ethylene diamine tetraacetic acid (EDTA), diethylene triamine pentaacetic acid (DTPA), triethylene tetraamine hexaacetic acid (TTHA), and tetraethylene pentaamine heptaacetic acid), more preferably DTPA and EDTA. Examples of cyclic chelating moieties used in such imaging agents include polyazamacrocyctic compounds (see, for example, Sherry et al., 1992, 1994, supra) such as 1,4,7,10-tetra-azacyclododecane-1,4,7,10-tetraacetic acid (DOTA).

Bi-functional calixarene conjugates useful for both MRI and CT are also contemplated. For example, calixarene conjugates may be prepared which have at least two imaging moieties, of which at least one is a CT imaging moiety and at least one is an MR imaging moiety.

B. Preparation of Calixarene Conjugates

The calixarene conjugates of the invention may be prepared by a number of strategies. One strategy involves first the formation of a calixarene backbone followed by the derivatization of the calixarene backbone to yield the calixarene conjugate. A simple and easily synthesized calixarene (e.g., wherein $R^1$ is —OH, $R^4$ is —$C(CH_3)_3$, and J is —OH) can be first activated to provide a reactive functional group. An imaging moiety can then, if necessary, be activated to also possess a reactive functional group. The activated calixarene and the activated imaging moiety compound can then be reacted together to yield a calixarene conjugate comprising an imaging moiety attached to a calixarene backbone. The term "reactive functional group" as used herein denotes a chemical group which is capable of reacting with another chemical group, which may also be a "reactive functional group", to form a covalent bond.

For example, an activated calixarene possessing a sulfonyl halide group, such as sulfonyl chloride group at the 4-position, is reacted with an activated imaging moiety compound possessing a reactive amino group, such as N-(2'-aminoethyl)-2,4,6-triiodo-3-aminobenzamide, to yield a calixarene conjugate possessing a sulfonamide linkage (—S(=O)$_2$—NH—). The sulfonamide linkage may then be further derivatized, for example, by using propane-1,3-sultone and base, to yield a water soluble calixarene conjugate salt. See, for instance, Example 1 below.

A wide variety of pairs of reactive functional groups may be employed to effect conjugation of the calixarene with an imaging moiety. Examples of preferred pairs of reactive functional groups include a sulfonyl halide (—SO$_2$X) and an amino group (—NH$_2$) which yield a sulfonamide linkage (—SO$_2$NH—); an amino group (—NH$_2$) and an isothiocyanato group (—NCS) which yield a thiourea linkage (—NH—C(=S)—NH—); an amino group (—NH$_2$) and an active ester group (—C(=O)OR*, wherein R* is an activating group, such as succinimidyl or 1-benzotriazolyl, the latter yielding a water soluble leaving group) or an anhydride (—C(=O)OC(=O)R, wherein R is a group such as aryl or alkyl, which leaves in the acid form when reacted with the amino group) or an acid halide (—C(=O)X, wherein X is halide such as Cl, Br, or I, preferably Cl) which yield an amide linkage (—NH—C(=O)—); and an amino group (—NH$_2$) and an isocyanato group (—NCO) which yield a urea linkage (—NH—C(=O)—NH—).

Additional examples of pairs of reactive functional groups include an amino group (—NH$_2$) and an amidine ester group (—C(=NY)OZ) which yield an amidine linkage (—NH—C(=NR)—); an amino group (—NH$_2$) and a haloformate group (—OC(=O) X) which yield a carbamate linkage (—NH—C(=O)O—); a sulfhydryl group (—SH) and a haloacetyl group (—C(=O) CH$_2$X) which yield a —SCH$_2$C(=O)—linkage; a sulfhydryl group (—SH) and an alkyl halide group (—alkyl—X) or an alkyl sulfonate group (—S(=O)$_2$O—alkyl) which yield a thioether linkage (—S—); and a sulfhydryl group (—SH) and another sulfhydryl group (—SH) which yield a disulfide linkage (—SS—); wherein X (halide) is as defined above, Y is a pharmacologically acceptable group such as hydrogen or methyl and Z is a group such as aryl or alkyl which leaves in the alcohol form when reacted with the amino group.

Included in the term "reactive functional groups" are those functional groups which can be activated by known methods. For example, active esters (—C(=O)OR*, wherein R* is, as defined above and acid halides (—C(=O)X, wherein X (halide) is as defined above may be derived from carboxylic acids.

As to which member of the pair of reactive functional groups is present on either the activated calixarene or the activated imaging moiety compound, the choice may be governed by synthetic convenience and ease of purification.

Both the calixarene 1-position and 4-position may be variously derivatized to yield reactive functional groups by known methods. For example, the more versatile 4-position may be derivatized to yield reactive functional groups such as —SO$_2$Cl —NH$_2$, —NO$_2$, —SH, —CN, —COOH, and the like. The —OH group in the 1- position of simple calixarenes may be used as a reactive functional group, or it may be derivatized to yield, inter alia, reactive functional groups such as —O(CH$_2$)$_n$CO$_2$R and O(CH$_2$)$_n$SO$_3$M where M is a metal such as sodium or potassium and R is an alkyl or substituted alkyl or M.

Many suitable activated imaging moieties are known in the art. For example, the NSP compound 4-amino-2,2,6,6,-tetramethyl-1-piperidinoxyl (also known as 4-amino-TEMPO) and the iodinated compound N-(2'-aminoethyl)-2,4, 6-triiodo-3-aminobenzamide both possess amino groups which may react with sulfonyl halide groups. Similarly, the fluorinated compound C(CF$_3$)$_3$CH$_2$CH$_2$Br possesses an alkyl halide group which may react with a phenolic —OH group.

Activated imaging moieties may also be obtained by derivatizing known compounds, including, for example, known imaging agents, to yield compounds possessing a reactive functional group. For example, a chelating agent useful in the formation of paramagnetic metal complexes, such as DTPA, may be derivatized by known methods to yield a reactive isothiocyanato group (—NCS) (see Example 4 below). Similarly, the chelating agent DOTA (1,4,7,10-tetra-azacyclododecane-1,4,7,10-netraacetic acid) may be derivatized by known methods, for example, to yield the 2-(p-isothiocyanatobenzyl) derivative.

In some instances, one or both of the calixarene and imaging moiety compound need not be activated to permit conjugation. For example, calixarene conjugates may be formed by reaction of simple calixarenes wherein R$^1$ is —OH and R$^4$ is —H with imaging moiety compounds such as triiodobenzoylchloride (to yield a CT imaging agent) or (CF$_3$)$_3$C(CH$_2$)$_s$C(=O)X (tO yield an MR imaging agent wherein s is about 1 to 5 and X (halide) is Cl, Br, or I). In the latter example, the phenyl ring of the calixarene with the —H in the R$^4$ position reacts with the acyl (Friedel-Crafts reaction), resulting in the formation of a covalent bond.

An alternative strategy for the formation of calixarene conjugates involves the derivatization of a calixarene backbone. For example, a simple calixarene which has been derivatized to have a haloalkyl group (e.g. —CH$_2$C$_1$) at the 4-position may be reacted under conditions described by Rogers et al. (1993, U.S. Pat. No. 5,234,680; perfluoroisobutylene with cesium fluoride in monoglyme) to yield a calixarene conjugate containing the MR imaging moiety —C(CF$_3$)$_3$.

Yet another alternative strategy for the formation of calixarene conjugates involves first derivatizing precalixarene monomers followed by the formation of a calixarene structure. For example, perfluoro-tert-butylphenol monomers may be prepared by reacting p-fluoro-nitrobenzene with Cs$^+$C(CF$_3$)$_3$$^-$ in monoglyme to yield nitrobenzene, followed by reduction of the nitro group to an amino group, diazotization of the amino group to yield a diazonium salt, and hydrolysis to yield a hydroxy group. In the same manner that 4-tert-butylphenol is reacted with formaldehyde to yield a simple calixarene, 4-perfluoro-tert-butylphenol may be reacted with formaldehyde to yield a calixarene conjugate wherein the imaging moiety is perfluoro-tert-butyl (—C(CF$_3$)$_3$) in the 4-position.

The molecular weight of the resulting calixarene conjugate, and therefore the nature and degree of the imaging moieties and spectator substituents, may be selected to optimize in vivo behavior. For example, Guerbet et al. (1993, WO 93/10824) discuss the beneficial aspects of high molecular weight CT imaging agents for the blood pool. Imaging agent molecular weights of at least about 3,000 g/mol, more preferably at least about 5,000 g/mol, yet more preferably at least about 6,500 g/mol are desirable. Although there remains contention in the art as to the existence of an upper limit for preferred blood pool imaging agent molecular weights, such an upper limit may be less than about 15,000 g/mol, more preferably less than about 13,000 g/mol, yet more preferably less than about 11,500 g/mol.

Note that the molecular weight of the simple calixarene wherein R$^1$ is —OH, R$^4$ is —C(CH$_3$)$_3$, J is —CH$_2$—, and n is 8, is approximately 1296 g/mol. The approximate molecular weights of the imaging agents described in Examples 1, 2, 3, 4, and 5 are, respectively, Compound (8): 7065 g/mol, Compound (13): 3858 g/mol, CompOund (15): 3796 g/mol, Compound (18): 7290 g/mol, and Compound (22): 9032 g/mol.

The calixarene conjugates of the invention may or may not be water-soluble, but preferably are water-soluble. The water-solubility of the calixarene conjugates may be influenced by the choice of the imaging moiety and/or spectator substituent. In particular, the imaging moiety and/or spectator substituent may be chosen to further comprise one or more chemical groups which influence water solubility of the calixarene conjugate.

Water solubility of the calixarene conjugates may be increased by incorporating chemical groups which are ionic or neutral. Conversely, incorporating chemical groups, such as hydrophobic groups, will reduce the overall water-solubility of the calixarene conjugate. Additionally, many nitroxyl containing CT imaging moieties are hydrophobic, and imaging agents comprising such imaging moieties will be less water-soluble. Also, neutral hydrophobic spectator groups such as, for example, the hydrocarbyl groups (e.g., alkyl, aryl, aralkyl, and alkaryl) described above may reduce overall water-solubility.

The number and choice of chemical groups may further be selected to influence the overall neutrality or charge of the calixarene conjugate. Although ionic species are often more water-soluble, neutral water-soluble species often afford more favorable osmolalities. Examples of such chemical groups include carboxylic acid, sulfonic acid, amino acid, sulfonic acid amine, ethanolamine, and amide.

The calixarene conjugates of the present invention may optionally be further conjugated to one or more targeting moieties, wherein the targeting moiety permits or enhances tissue or organ specificity, including, for example, kidney, liver, or tumor specificity. For example, further conjugation to yield a high molecular weight water soluble calixarene conjugate may permit targeting properties suitable for blood pool imaging. Also, further conjugation to a low molecular weight protein may permit kidney specificity, whereas further conjugation to metalloporphyrins may permit tumor (such as breast tumor) specificity. Imaging agent formulations comprising microemulsions of water-insoluble calixarene conjugates may permit liver specificity.

C. Methods of Imaging

The methods of CT and MRI are well known in the art. See, inter alia, *The Contrast Media Manual*, (1992, R. W. Katzberg, Williams and Wilkins, Baltimore, Maryland), especially chapter 6 ("Contrast Media Use in Computed Tomography") and chapter 13 ("Magnetic Resonance Contrast Agents").

Typically, an effective amount of an imaging agent formulation comprising the calixarene conjugate and pharmaceutically acceptable carrier is administered to the patient, and the patient, or a portion of the patient, is imaged. The term "effective amount", as used herein, denotes a non-toxic amount sufficient to enhance or alter the CT or MRI image obtained, more particularly, an amount which permits better visualization of the organs and/or tissues being imaged. Preferably the patient is an animal; more preferably, the patient is a mammal; most preferably the patient is a human.

The imaging agents of the present invention may be variously administered by any suitable route, including, for example, orally, for imaging of the upper gastrointestinal tract; rectally, for imaging of the lower gastrointestinal tract including the colon; nasally, for imaging of the nasal and communicating passages; vaginal, for imaging of the fallopian tubes and communicating passages; parenteral (including subcutaneous, intramuscular, intravenous, intradermal and pulmonary), for imaging of internal organs, tissues, tumors, and the like. It will be appreciated that the preferred route will vary with the organs or tissues to be imaged. Preferred routes of administration include parenteral and oral, more preferably intravenous.

While it is possible for the imaging agent to be administered alone, it is preferable to present it as a pharmaceutical formulation comprising at least one imaging agent compound, together with one or more pharmaceutically acceptable carriers, such as diluents or excipients which may include, for example, fillers, extenders, wetting agents, disintegrants, surface-active agents, or lubricants, depending on the nature and mode of administration and the dosage forms. Each carrier must be "acceptable" in the sense of being compatible with the other ingredients of the formulation and not injurious to the patient. The pharmaceutical formulation may optionally include other diagnostic or therapeutic agents. Techniques and formulations may be found, for example, in *Remington's Pharmaceutical Sciences*, Mack Publishing Co., Easton, Pa. (latest edition).

Formulations of the present invention suitable for oral administration may be presented as a solution or suspension in an aqueous or non-aqueous liquid; or as an oil-in-water liquid emulsion; or a water-in-oil liquid emulsion. Alternatively, formulations can be administered as capsules, cachets or tablets, each containing a predetermined amount of the imaging agent; powder; granules; or paste.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more tissues or organs.

The formulations may be presented in unit-dose or multi-dose sealed containers, for example, ampules and vials, and may be stored in a freeze-dried (lyophilized) condition requiring only the addition of the sterile liquid carrier, for example water, for injections immediately prior to use. Extemporaneous injection solutions and suspensions may be prepared from sterile powders, granules or tablets.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents.

Compounds of the formula of the present invention may also be presented for use in the form of veterinary formulations, which may be prepared, for example, by methods that are conventional in the art.

For CT, dosages may be conveniently calculated as milligrams of halide, for example, iodine per kilogram of patient (abbreviated as mg(I)/kg). For parenteral administration, typical dosage volumes for an average human adult are 100–300 mL, preferably about 200 mL, with formulation concentrations of about 100–300 mg(I)/mL, preferably 200 mg(I)/mL. An average human patient of weight 70 kg may therefore receive about 571 mg(I)/kg for an overall dosage of about 40 g(I).

For MRI contrast agents, dosages will depend on the spin density, flow (diffusion and perfusion), susceptibility, and relaxivity (T1 and T2) of the imaging agent formulation. For MRI, dosages may be conveniently calculated as millimoles of contrast agent per kilogram of patient (abbreviated as mmol(A)/kg). For example, for parenteral administration, typical dosages may be 0.01 to 1 mmol(A)/kg.

Rates of administration are known in the art. Typical rates of administration are about 0.5 to 5 mL of formulation per second, more preferably about 1–3 mL/s. Imaging may begin before or after commencing administration, continue during administration, and may continue after administration. It will be appreciated that dosages, dosage volumes, formulation concentrations, rates of administration, and imaging protocols will be individualized to the particular patient and the examination sought, and may be determined by an experienced practitioner. Guidelines for selecting such parameters are known in the art (see, inter alia, Katzberg, 1992, supra).

D. Examples

Example 1

Synthesis of a Calixarene Conjugate e Useful for CT

The synthesis of compound (8) is described below and is shown schematically in FIG. 1. Compound numbers in parentheses refer to the structures shown in the Figures.

Compound (2): octa(1-hydroxy) octa(4-tert-butyl) calix[8]arene

Compound (2) was prepared according to the method described by Munch et al. (*Organic Synthesis,* 1989, 68:243–245.) A slurry of p-tert-butylphenol (Compound (1), 100.0 g, 0.67 mol), paraformaldehyde (35 g, 1.1 mol) and 2 mL of 10 N sodium hydroxide in xylene (600 mL) was placed in a 2 L, round bottomed, three-necked flask fitted with a Dean-Stark water collector and a mechanical stirrer. The slurry was heated in an atmosphere of argon to reflux with stirring. After 1 hr, a white precipitate started to separate. The reaction mixture was heated for 8 hr. The mixture was then cooled to room temperature and the precipitate filtered to remove unreacted components and by-products. The crude product was washed, in succession, with 400 mL portions of toluene, ether, acetone, and water and then dried under reduced pressure. The product was dissolved in chloroform and crystallized. The resultant crystals were separated by filtration and dried. Yield=70.5 g, 67%; purity in TLC ($SiO_2$), hexane/dichloromethane (8:2), Rf=0.55; NMR ($CDCl_3$)=1.23 (s, 72H t-butyl) , 3.55 and 4.42 (2d, 16H, $CH_2$) , 7.19 (s, 16H, aromatic) , 9.53 (s, 8H, OH) , δ ppm.

Compound (3): octa(1-hydroxy) calix[8]arene

Compound (3) was prepared according to the method described by Gutsche et al. (Tetrahedron, 1986, 42:1633–1640). A slurry of compound (2) (20.0 g, 0.015 mol), phenol (12.0 g, 0.124 mol) and anhydrous aluminum chloride (25 g, 0.186 mol) in toluene (300 mL) was stirred at room temperature for 1 hr in an argon atmosphere. The mixture was poured into 500 mL of water at 4° C. and stirred for 1 hr. The insoluble slurry thus formed (top layer), which contained the product with phenol, was separated from the aqueous (bottom) layer and the toluene was removed in a rotary evaporator. The slurry was then washed in succession with 100 mL acetone, 0.1 N hydrochloric acid, methanol, chloroform, acetone and ether, and then filtered and dried under reduced pressure. Yield=12.2 g, 98%; NMR (pyridine)=4.25 (s, br, 16H, CH2) , 6.85 (t, 8H, aromatic) , 7.19 (s, br, 16H, aromatic), 9.34 (s, br, 8H, OH) δ ppm.

Compound (4): octasodium octa (1-hydroxy) octa (4-sulfonato) calix [8]arene

Compound (3) (4.2 g, 0.0047 mol) was stirred with concentrated sulfuric acid (35 mL) and heated to 60° C. for 4 hr. The insoluble product was filtered through a glass filter and the solid was dissolved in 120 mL water. The solution was neutralized with excess barium carbonate (10.0 g) to pH 6–7 and was subsequently filtered. The filtrate was adjusted to pH 8–9 with a calculated amount of sodium carbonate (1.4 g). The aqueous solution was lyophilized to produce a colorless powder (3.8 g). The powder was redissolved in water (10 mL) and diluted with equal amounts of ethanol. The product in the sodium salt form was filtered and dried. Yield=3.8 g, 70%; NMR ($D_2O$)=3.9 (s, 16H, $CH_2$), 7.45 (s, i6H, aromatic) δ ppm.

Compound (5): octasodium octa (1-methoxy) octa (4-sulfonato) calix [8]arene

Compound (5) was prepared according to the method described by Shinkai et al. (*J. Amer. Chem. Soc.,* 1986, 108:2409–2416). Compound (4) (3.2 g, 0.002 mol) was dissolved in sodium hydroxide solution (15 mL, 2.24 g, 0.056 mol) and dimethylsulfoxide (50 mL) was added to the mixture. Iodomethane (8.4 g, 0059 mol) in dimethylsulfoxide (10 mL) was added and the solution was heated to 50°–55° C. for 24 hr. The mixture was cooled and diluted with ethanol (200 mL). The solid product was filtered and dried. The solid was subsequently dissolved in 10 mL water and diluted with 15 mL ethanol. The precipitated solids were filtered and dried. This procedure was repeated three times to remove the excess sodium iodide. The product formed pale yellow crystals. Yield=1.82 g, 60%; NMR ($D_{2O}$)=3.27 (s, 24H, $OCH_3$), 4.08 (s, 16H, $CH_2$), 7.50 (s, 16H, aromatic) δ ppm.

Compound (6): octa (1-methoxy) octa (4 -chlorosulfonyl) calix [8 ]arene

Compound (6) was prepared according to the method described by Shinkai et al. (*Bull. Chem. Soc. Jpn.,* 1990, 63:1272–1274). Compound (5) (1.5 g, 8 mmol) was refluxed with thionyl chloride (15 mL) in the presence of a few drops of dimethylformamide. After 4 hr, the reaction mixture was cooled and poured into ice-water. The precipitate was recovered by filtration and extracted into chloroform. The chloroform layer was dried with $Na_2SO_4$ and filtered. Removal of the chloroform followed by crystallization produced pale yellow crystals. Yield=64%, mp=286° C. (dec); NMR ($D_2O$)=3.62 (<s, 24H, $OCH_3$), 4.21 (s, 16H, $CH_2$), 7.68 (s, 16H, aromatic) δ ppm.

Compound 7 ):

The reagent, N-(2'-aminoethyl)-3-amino-2,4,6,-triiodobenzamide, is prepared from 3-amino-2,4,6-triiodobenzoic acid and ethylene diamine via the carboxylic acid chloride. Compound (7) is then prepared by a method analogous to the one described by Shinkai et al. (1990, supra) by reaction of Compound (6) (0.1 g, 0.05 mmol) with 2 equivalents of the reagent N-(2'-aminoethyl)-3-amino-2,4, 6,-triiodobenzamide 10.51 g, 0.89 mmol) in 5 mL pyridine.

Compound (8 ):

Compound (7) in dimethylsulfoxide is treated with excess sodium hydride and propane-1,3-sultone to obtain Compound (8) using a method analogous to that described by Shinkai et al. (*J. Chem. Soc. Perkin Trans. I,* 1989, 2039–2045).

Example 2

Synthesis of a Calixarene Conjugate Useful for $^{19}F$ MRI

Figure 2:
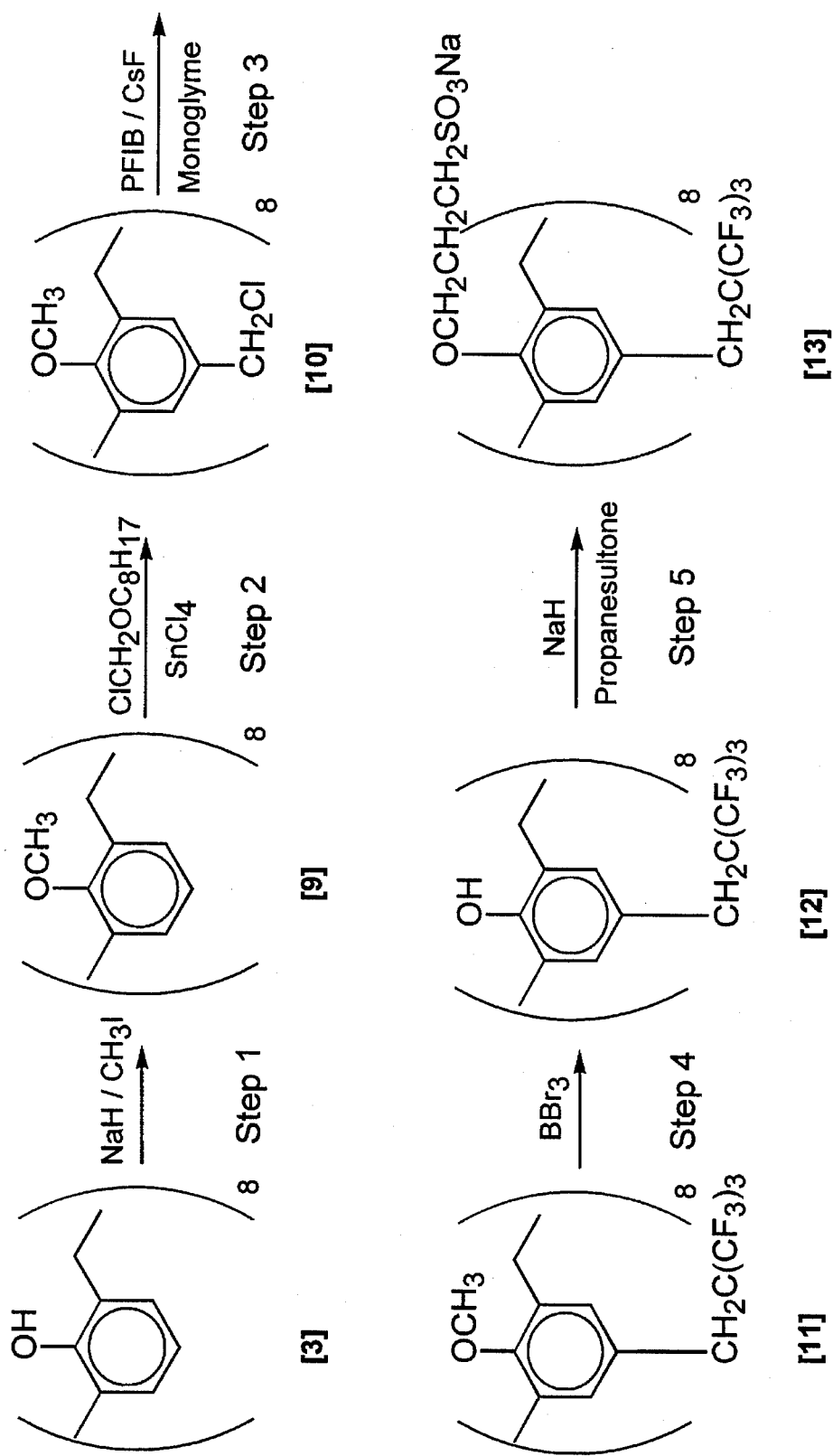
FIG. 2 is a flow chart that illustrates a synthetic route for the preparation of a calixarene conjugate having a fluorinated MR imaging moiety.

The synthesis of compound (13) is described below and is shown schematically in FIG. 2. Compound numbers in parentheses refer to the structures shown in the Figures.

Compound (9): octa (1-methoxy) calix [8]arene

Compound (9) was prepared according to the method described by Gutsche et al. (1986, supra). A mixture containing compound (3) (4.5 g, 0.0053 mol), sodium hydride (80% in oil, 7.2 g, 0.188 mol) in tetrahydrofuran (200 mL) was prepared and reacted at room temperature to form the sodium salt. Then dimethylsulfate (26.6 g, 0.211 mol) in DMF (50 mL) was added. The resultant mixture was heated at 70° C. for 20 hr. It was then cooled and the excess sodium hydride was decomposed with methanol (25 mL). Methanol, tetrahydrofuran and DMF were removed under reduced pressure. The residue thus formed was washed with water (150 mL) and methanol (100 mL) to yield the crude product which was then passed through a silica gel column (45 g). The product was eluted with a mixture of hexane and ethyl acetate (1:1) followed by dichloromethane to obtain pale yellow crystals. Recrystallization from methanol and chloroform yielded 3.61 g, 71%. NMR (CDCl$_3$)=3.5 (s, 24H., OCH$_3$), 4.0 (s, 16H, CH2), 6.8 (s, 8H aromatic) δ ppm.

Compound (10): octa(1-methoxy) octa(4-chloromethyl) calix[8]arene

Compound (10) is prepared according to the method described by Aimi et al. (*Tetrahedron*, 1989, 45:2177–2182). Compound (9) in chloroform solution is reacted with stannic chloride at −10° C. for 50 min. The reaction mixture is poured into water and after extraction and removal of chloroform, the product is crystallized to produce compound (9) in pure form.

Compound (11): octa (1 -methoxy) octa{4-[(perfluoro- tert-butyl)methyl]}calix[8]arene Compound (11) is prepared according to the method described by Rogers et al. (1993, U.S. Pat. No. 5,234,680). Compound (10) in monoglyme (CH$_3$O-CH$_2$CH$_2$-OCH$_3$) is reacted with perfluoroisobutylene and cesium fluoride at room temperature for 20 hr and is worked-up by filtering off the cesium bromide and removing the monoglyme solvent. The product is extracted in chloroform and the solvent is dried and then removed in a rotary evaporator. The residue is recrystallized to yield compound (11).

Compound (12): octa (1-hydroxy) octa{4- [(perfluoro- tert-butyl)methyl]}calix[8]arene Compound (12) is prepared according to the method described by McOmie et al. (*Tetrahedron*, 1968, 24:2289–2292), for de-methylation of methyl ethers. Compound (11) is dissolved in dichloromethane and reacted with excess boron tribromide at −60° C. to −40° C. for 3 to 4 hr. The mixture is poured into dilute hydrochloric acid and the dichloromethane layer is separated and the solvent is dried and then removed. The residue is purified by crystallization and/or chromatography to yield compound (12).

Compound (13): octasodium octa{1-(3-sulfonatopropoxy) } octa{4-[(perfluoro-tert-butyl)methyl]}calix [8 ]arene Compound (13) is prepared by the method described by Shinkai et al. (1989, supra). Compound (12) in tetrahydrofuran is treated with excess sodium hydride and propane-1, 3-sultone to obtain compound (13).

Example 3

Figure 3:
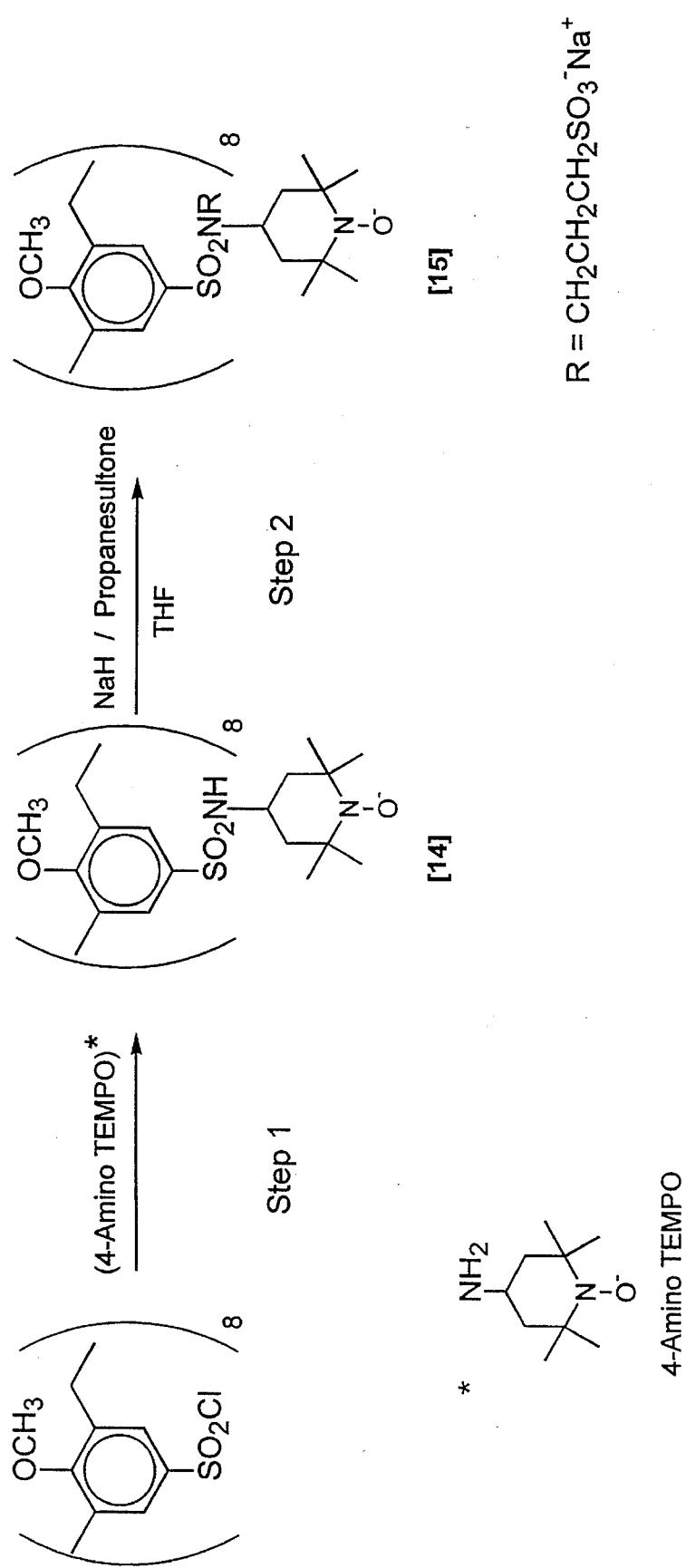
FIG. 3 is a flow chart that illustrates a synthetic route for the preparation of a calixarene conjugate having a nitroxyl spin labeled MR imaging moiety.

Synthesis of a Calixarene Conjugate Comprising an Organic Paramagnetic Group Useful for MRI The synthesis of compound (15) is described below and is shown schematically in FIG. 3. Compound numbers in parentheses refer to the structures shown in the Figures.

Compound (14):

The compound (14) is prepared according to similar procedures described earlier by Shinkai et al. (1990, supra). Compound (6) is reacted with excess 4-amino-TEMPO (4-amino-2,2,6,6,-tetramethyl-1-piperidinoxyl, Aldrich Chemical Company, Milwaukee, Wis.) in chloroform. Compound (14) is isolated and purified by crystallization. Compound 15):

Compound (14) in tetrahydrofuran is reacted with excess sodium hydride and propane-1,3-sultone as described by Shinkai et al. (1990, supra) to obtain the compound (15) as a water soluble sodium salt.

Example 4

Figure 4:
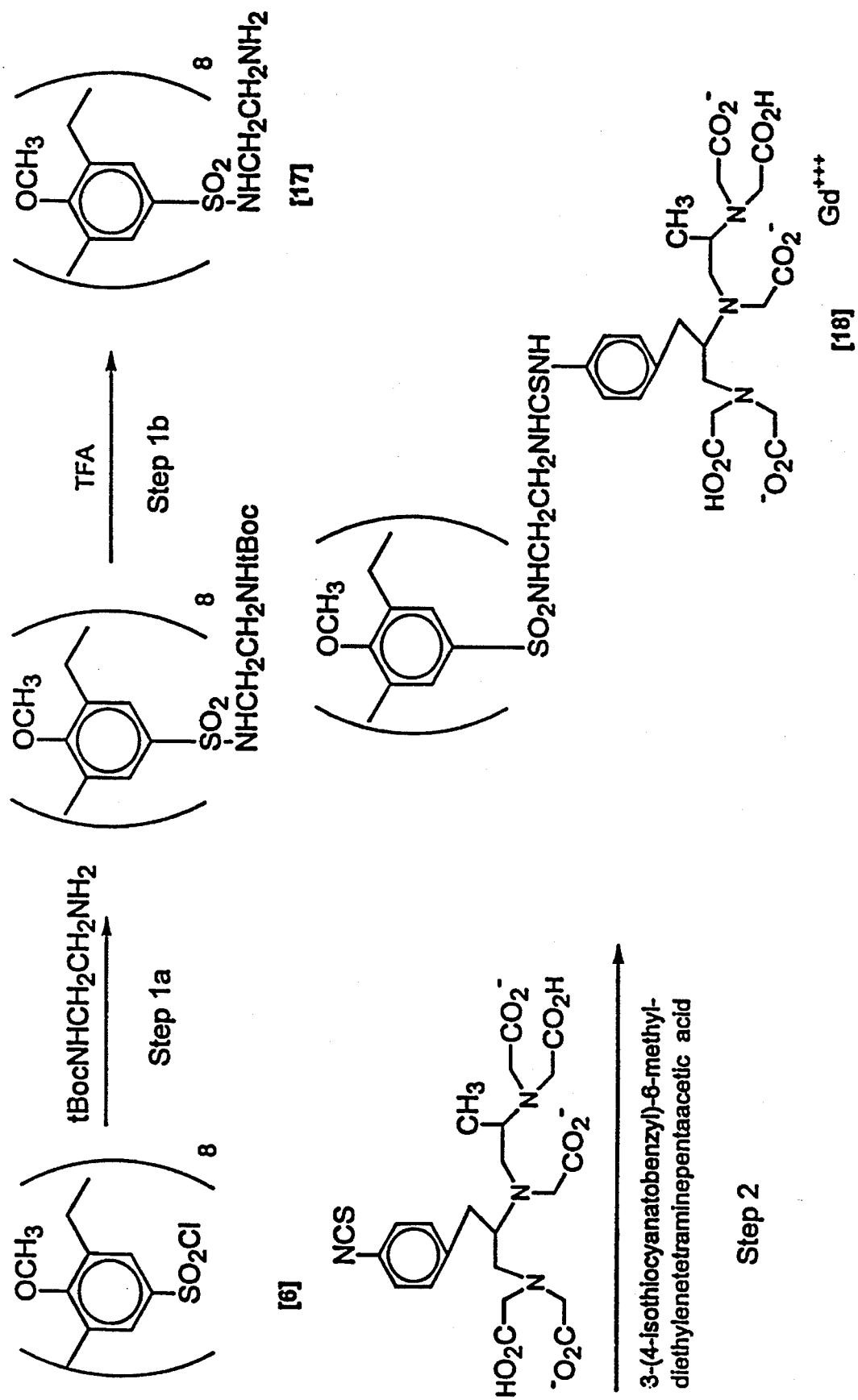
FIG. 4 is a flow chart that illustrates a synthetic route for the preparation of a calixarene conjugate having a paramagnetic metal chelate MR imaging moiety.

Synthesis of Calixarene Conjugates Comprising a Paramagnetic Metal Complex Moiety Useful for MRI The synthesis of compound (18) is described below and is shown schematically in FIG. 4. Compound numbers in parentheses refer to the structures shown in the Figures.

Compound 16 ):

Compound (6) is treated with N-(tert-butoxycarbonyl)ethylenediamine in a suitable solvent at room temperature as described by Essian et al. (*J. Med. Chem.*, 1988, 31:898–891) to yield compound (16).

Compound (17): octa (1-methoxy) octa{4-[N-(2'-amino) ethyl) sulfonamido]}calix [8]arene Compound (16) is converted to Compound (17) in free-base form by reacting with trifluoroacetic acid in a manner analogous to that described by Betebenner et al. (*Bioconjugate. Chem.*, 1991, 2:117–123).

Compound (18): DTPA Conjugate

The reagent, 3-(4-isothiocyanatobenzyl)-6 methyl-diethylene-tetraaminepentaacetic acid, is prepared as described by Brechbiel et al. (*Bioconjugate Chemistry*, 1990, 1(1):59–68) and reacted with compound (17) in dichloromethane at room temperature as described by Weiner et al. (*Mag. Res. Med.*, 1994, 31:1–8) to give compound (18).

Example 5

Synthesis of Bifunctional Calixarene Conjugates Useful For Both MRI and CT

Figure 5:
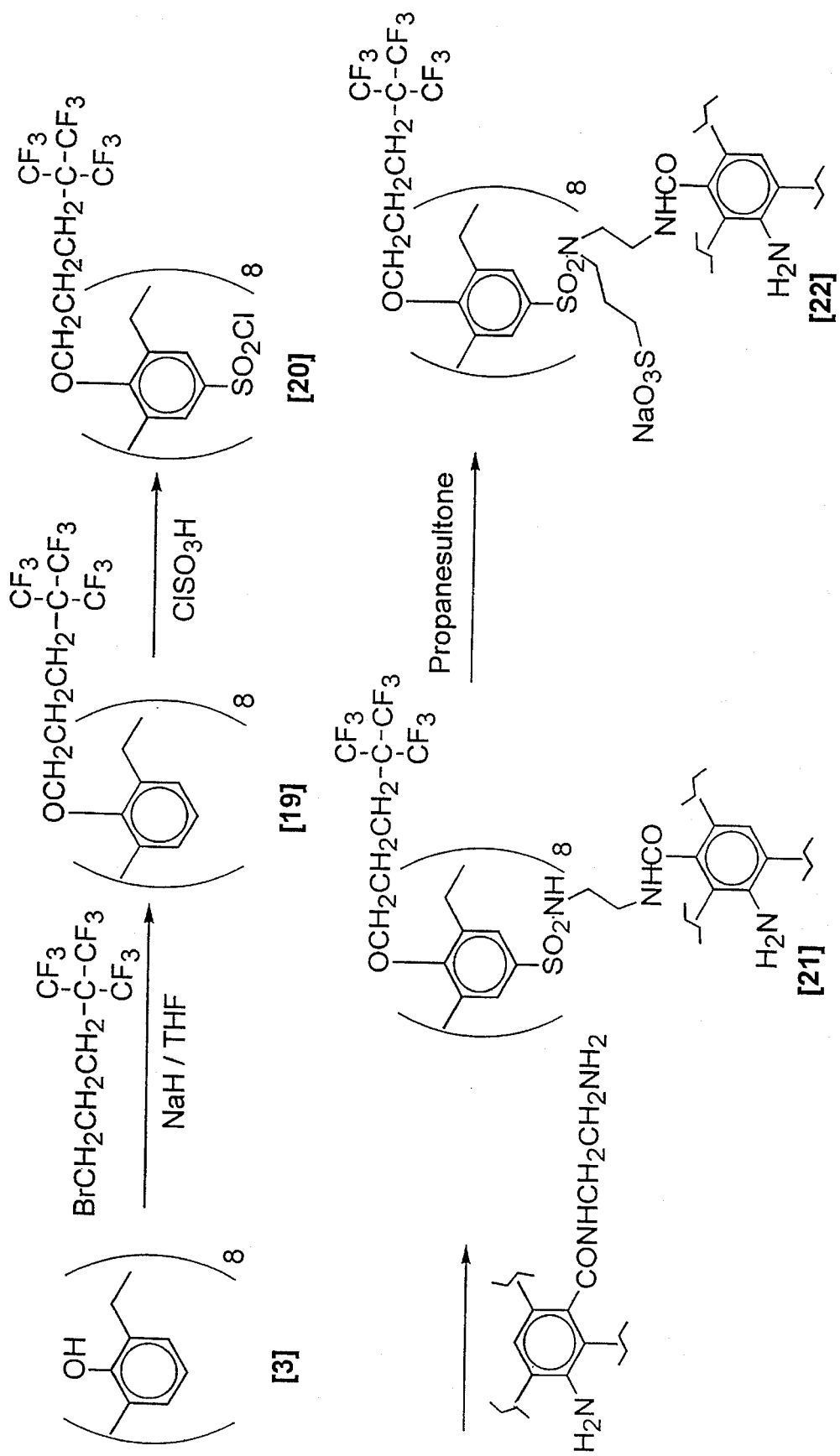
FIG. 5 is a flow chart that illustrates a synthetic route for the preparation of a bifunctional calixarene conjugate having both a iodinated CT imaging moiety and a fluorinated MR imaging moiety.

The synthesis of compound (22) is described below and is shown schematically in FIG. 5. Compound numbers in parentheses refer to the structures shown in the Figures.

Compound (19): octa{1-[3-(perfluoro-tert-butyl)propoxy]} calix [8 ]arene

Compound (19) is prepared by a method analogous to the one described by Shinkai et al. (1990, supra). Compound (3) is converted to the sodium salt with excess sodium hydride in a solvent such as tetrahydrofuran or dimethylformamide and then reacted 1-bromo-3-(perfluoro-tert-butyl)propane to furnish Compound (19) which is purified by crystallization or chromatography. 1-bromo-3-(petfluoro-tert-butyl)propane is prepared by reacting perfluoroisobutylene and cesium fluoride in a solvent like monoglyme with excess dibromopropane as described by Rogers et al. (1993, U.S. Pat. No. 5,234,680).

Compound (20): octa{1-[3- (perfluoro-tert-butyl)propoxy]} octa (4-chlorosulfonyl) calix [8]arene Compound (20) is prepared by reacting Compound (19) with excess chlorosulfonic acid in a solvent like chloroform. After stirring the mixture at room temperature for 6–8 hours, the reaction mixture is poured into ice water and the product obtained from the organic layer after suitable workup and crystallization.

Compounds (21 ) and (22 ):

Compounds (21) and (22) are prepared from compound (20) by reactions analogous to ones described above for the preparation of compounds (7) and (8), respectively.

Example 6

In Vivo CT Imaging

Imaging agents for CT are prepared as described in Examples 1 and 5 and suspended in a pharmaceutically acceptable carrier. CT imaging is carried out by standard procedures using commercially available equipment. The x-ray beam energy is typically 120 KeV although dual energy beam systems are available. X-ray CT is an inherently two-dimensional imaging method that acquires transaxial images of any region of the human body, provided that region is located within the x-ray beam-detector gantry. Conventional CT scanners use fixed parameters for slice Described in Table 1 are three exemplary imaging dosages for a 70 kg human subject using the compounds of Examples 1 to 4.

TABLE 1

| Imaging Agent | Molecular Weight, g/mol | Dosage A (Amount to Administer) | Dosage B (Amount to Administer) | Dosage C (Amount to Administer) |
|---|---|---|---|---|
| Example 1 Compound 8 | 7065 (43.14% I) | 100 mg I/Kg (16.25 g) | 200 mg I/Kg (32.48 g) | 300 mg I/Kg (48.72 g) |
| Example 2 Compound 13 | 3858 (35.5% $^{19}$F) | 100 mg $^{19}$F/Kg (19.7 g) | 250 mg $^{19}$F/Kg (49.3 g) | 500 mg $^{19}$F/Kg (98.7 g) |
| Example 3 Compound 15 | 3796 (8 spins*/molecule) | 1.5 mmol (1 spin per molecule)/Kg (49.9 g) | Not Determined | Not Determined |
| Example 4 Compound 18 | 7290 (1258 mg Gd/mmol) | 0.1 mmol Gd/Kg (6.38 g) | Not Determined | Not Determined |

*A "spin" is the result of the presence of one unpaired electron. Thus, a molecule such as compound 15, of Example 8, which contains 8 nitroxyl free radicals per molecule is said to contain 8 spins per molecule.

thickness; the in-plane resolution can be adjusted within pre-determined parameters set by the manufacturer (e.g., 256×256 or 512 pixel resolution and scan time, which is a function of the resolution.) Spiral or helical scanning CT units allow for more options of slice thickness and typically have shorter scan times (about 1 second/slice).

The subject to be imaged is placed on a CT patient platform ("couch"). An initial alignment using the positioning system of the scanner and external anatomic reference pints in the subject is done. A "scout" image is done to determine if the subject is properly located within the CT gantry; if not, the subject is repositioned by remotely controlling the travel of the patient platform to obtain the desired location. This is repeated until desired alignment is achieved.

Typically, a series of precontrast images are obtained. Following administration of the contrast agent, the CT examination is performed while the contrast agent is present in the region being imaged. Imaging dosages are calculated as described in Example 8.

Example 7

In Vivo MRI

Imaging agents for MRI are prepared as described in Examples 2 to 5 and suspended in a pharmaceutically acceptable carrier. Proton ($^1$H) and/or fluorine imaging are carried out using standard procedures and commercially available equipment. Proton imaging can be performed with the following parameters: Repetition time (TR)=1 second, echo time (TE)=18 milliseconds, image data matrix=128× 128, number of excitations (NEX)=2, field of view (FOV)= 128 nm, and slice thickness=2.5 or 5.0. Fluorine imaging can be performed with the following parameters: TR=1 second, TE=18 milliseconds, image data matrix=64×64, NEX=32, FOV=128 nm.

Proton and fluorine MRI are done before and after administration of the contrast agent. When using fluorine-containing imaging agents, such as those described in examples 2 and 5, proton MRI is used to provide anatomic markers for assessment of the fluorine images. Imaging dosages are calculated as described in Example 8.

Example 8

Imaging Dosage Calculations

Imaging dosages will depend on the solubility of the imaging agent, the route of administration, the carrier vehicle, the site to be imaged and the method of imaging.

We claim:
1. A calixarene conjugate comprising:
   (a) a calixarene backbone; and
   (b) at least one MAGNETIC RESONANCE imaging moiety linked thereto.
2. The calixarene conjugate of claim 1 wherein the conjugate has at least two imaging moieties, wherein at least one moiety is a CT imaging moiety and at least one moiety is a MR imaging moiety.
3. A calixarene conjugate of the formula:

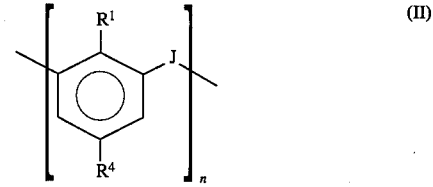

(II)

wherein at least one of the $R^1$ and $R^4$ substituents comprises A MAGNETIC RESONANCE imaging moiety, the remaining $R^1$ and $R^4$ substituents, if any, are spectator groups, J is an ortho-linker, and n is an integer from 4 to 8.
4. The calixarene conjugate of claim 3, wherein said ortho-linker is —CH$_2$—.
5. The calixarene conjugate of claim 3, wherein n=4.
6. The calixarene conjugate of claim 3, wherein all the $R^1$ groups comprise a magnetic resonance imaging moiety.
7. The calixarene conjugate of claim 3, wherein all the $R^4$ groups comprise A MAGNETIC RESONANCE imaging moiety.
8. The calixarene conjugate of claim 3, wherein said MR imaging moiety comprises four or more fluorine atoms.
9. The calixarene conjugate of claim 8, wherein said fluorine atoms are present as part of —CF$_3$ groups.
10. The calixarene conjugate of claim 9, wherein said fluorine atoms are present as part of one or more —C(CF$_3$)$_3$ groups.
11. The calixarene conjugate of claim 3, wherein said MR imaging moiety comprises at least one nitroxyl spin labeled moiety.
12. The calixarene conjugate of claim 11, wherein said nitroxyl spin labeled moiety comprises a piperidinoxyl moiety.
13. The calixarene conjugate of claim 3, wherein said MR imaging moiety comprises at least one metal chelate moiety.

14. The calixarene conjugate of claim 13, where said metal chelate moiety comprises a DTPA moiety.

15. The calixarene conjugate of claim 13, where said metal chelate moiety comprises a Gd(III) ion.

16. An imaging agent formulation comprising:
   (a) a calixarene conjugate comprising:
      a calixarene backbone, and
      at least one MR imaging moiety linked thereto; and
   (b) a pharmaceutically acceptable carrier.

17. A method of MRI comprising:
   (a) administering an effective amount of a calixarene conjugate having at least one MR imaging moiety to a patient; and
   (b) acquiring an MR image of at least a portion of the patient while the calixarene conjugate is present in the patient.

* * * * *